(12) United States Patent
Burt

(10) Patent No.: US 9,968,257 B1
(45) Date of Patent: May 15, 2018

(54) VOLUMETRIC QUANTIFICATION OF CARDIOVASCULAR STRUCTURES FROM MEDICAL IMAGING

(71) Applicant: Hälsa Labs, LLC, Windermere, FL (US)

(72) Inventor: Jeremy Burt, Windermere, FL (US)

(73) Assignee: Halsa Labs, LLC, Windermere, FL (US)

( * ) Notice: Subject to any disclaimer, the term of this patent is extended or adjusted under 35 U.S.C. 154(b) by 0 days. days.

(21) Appl. No.: 15/711,193

(22) Filed: Sep. 21, 2017

Related U.S. Application Data

(60) Provisional application No. 62/529,277, filed on Jul. 6, 2017.

(51) Int. Cl.
 *A61B 5/00* (2006.01)
 *A61B 5/055* (2006.01)
 *A61B 5/02* (2006.01)

(52) U.S. Cl.
 CPC ........ *A61B 5/0044* (2013.01); *A61B 5/02007* (2013.01); *A61B 5/055* (2013.01); *A61B 2576/023* (2013.01); *G06T 2207/30048* (2013.01)

(58) Field of Classification Search
 CPC .... A61B 5/0044; A61B 5/02007; A61B 5/055
 See application file for complete search history.

(56) References Cited

U.S. PATENT DOCUMENTS

| | | |
|---|---|---|
| 2010/0067760 A1 | 3/2010 | Zhang et al. |
| 2014/0022250 A1 | 1/2014 | Mansi et al. |
| 2015/0178938 A1 | 6/2015 | Gorman, III et al. |
| 2016/0098833 A1 | 4/2016 | Tsadok et al. |
| 2017/0109881 A1 | 4/2017 | Avendi et al. |
| 2017/0140236 A1* | 5/2017 | Price .................... G06K 9/2081 |
| 2017/0287137 A1* | 10/2017 | Lin ....................... G06T 7/0081 |

OTHER PUBLICATIONS

Kuppahally, Suman S., et al., "Left atrial strain and strain rate in patients with paroxysmal and persistent atrial fibrillation relationship to left atrial structural remodeling detected by delayed-enhacement mri," Circulation: Cardiovascular Imaging, vol. 3, No. 3, 2010.

(Continued)

*Primary Examiner* — Edward Park
(74) *Attorney, Agent, or Firm* — Fox Rothschild LLP; Robert J. Sacco; Carol E. Thorstad-Forsyth

(57) ABSTRACT

A computing system accesses complementary image data of a biological tissue structure (BTS), which can include a human cardiovascular structure. The complementary image data is comprised of two-dimensional images which represent different views of the BTS respectively aligned with a plurality of distinct image planes. A plurality of separate convolutional neural networks (CNNs) are used to respectively process each of the plurality of two-dimensional images. Each CNN determines a probability map which is then adaptively fused into a single segmented output. A contouring operation is automatically performed to calculate at least one clinical measurement and/or create at least one 3D volume.

23 Claims, 8 Drawing Sheets

(56) References Cited

OTHER PUBLICATIONS

Daoudi, Abdelaziz, et al., "Automatic segmentation of the left atrium on ct images," in International Workshop on Statistical Atlases and Computational Models of the Heart, Springer 2013, pp. 14-23.

Tobon-Gomez, et al., "Benchmark for algorithms segmenting the left atrium from 3d ct and mri datasets," IEEE TMI, vol. 34, No. 7, 2015.

Stender, Birgit, et al., "Model-based segmentation of the left atrium in ct and mri scans," in International Workshop on Statistical Atlasses and Computational Models of the Heart, Springer 2013.

Noh, Hyeonwoo, et al., "Learning deconvolution network for semantic segmentation," in Proceedings of the IEEE International Conference on Computer Vision, 2015, pp. 1520-1528.

de Br'ebisson, A., et al., "The z-loss: a shift and scale invariant classification loss belonging to the spherical family," arXiv preprint arXiv: 1604.08859, 2016.

Zuluaga, Maria A., et al., "Multi-atlas propagation whole heart segmentation from mri and cta using a local normalised correlation coefficient criterion," in International Conference on FUnctional Imaging and Modeling of the Heart, Springer 2013.

Peng Peng, et al., "A review of heart chamber segmentation for structural and functional analysis using cardiac megnetic resonance imaging," Magma (New York, NY), vol. 29, pp. 155, 2016.

Poudel, Rudra PK, et al., "Recurrent fully convolutional neural networks for multi-slice mri cardiac segmentation," arXiv prepring arXiv:1608.03974, 2016.

Avendi, M.R., et al., "A combined deep-learning and deformable-model approach to fully automatic segmentation of the left ventricle in cardiac mri," Medical Image Analysis, vol. 30, pp. 108-119, 2016.

Gongning, L., et al., "A deep learning network for right venticle segmentation in short-axis mri," in Computing in Cardiology Conference (CinC), 2016 IEEE, 2016, pp. 485-488.

Kalinic, Hrvoje, 2008. "Atlas-Based Image Segmentation: A Survey," Technical report. Department of Electronic Systems and Information Processing, Universiy of Zagreb, Croatia.

"Cardiovascular diseases (cvds)," http://www.who.int/mediacentre/facatsheets/fs317/en/,2007, [online; accessed Jun. 30, 2017.

* cited by examiner

VOLUMETRIC QUANTIFICATION OF CARDIOVASCULAR STRUCTURES FROM MEDICAL IMAGING

CROSS-REFERENCE TO RELATED APPLICATIONS

This application claims priority to U.S. Patent Application No. 62/529,277 filed on Jul. 6, 2017. The content of the above application is incorporated by reference in its entirety.

BACKGROUND

Statement of the Technical Field

The inventive arrangements relate to medical imaging, and more particularly to methods and systems for quantitative image analysis of medical imaging.

DESCRIPTION OF THE RELATED ART

According to the world health organization, cardiovascular diseases (CVDs) are the first cause of death globally. About 7.7 million people died from CVDs in 2015, which was 31% of total global deaths from diseases. Almost 7.4 million of these deaths were due to the CVDs and about 6.7 million were due to the stroke. Extensive research and clinical applications have shown that radiology imaging has vital roles in non-invasive assessment, therapy planning, and prognosis of CVDs.

Non-invasive detection of cardiovascular disorders from medical imaging requires analysis of the cardiovascular system. On a clinical basis, a starting point for such evaluation is usually the acquisition of cardiovascular imaging obtained using echocardiography, computed tomography (CT) and/or magnetic resonance imaging (MRI) methods. The purpose of such imaging is to facilitate a determination of various cardiac performance characteristics, such as the amount or volume of blood contained in the atria, volume of blood in the ventricles, and also the thickness of the muscle of the heart. Furthermore, changes in mechanical properties of the heart regions (myocardium, atria, aorta, etc.) can be learned and tracked via non-invasive imaging of the heart (four dimensional (4D) MRI, for instance, gives volumetric heart in temporal domain where motion of the heart carries important information for potential abnormalities). For example, practitioners can take images from the point where the chamber is most full (end-diastolic volume or EDV) and most empty (end-systolic volume or ESV). The difference in volume in each condition thus obtained can then be subtracted to determine the amount of blood that has been ejected from that chamber (stroke volume). A ratio between the stroke volume and the end-diastolic volume is used to calculate the ejection fraction (EF), which serves as a good indication of how well a person's heart is working.

The ejection fraction or EF must be accurately calculated because it is an important consideration with respect to determining proper diagnosis and treatment. The current way of calculating EF involves viewing the cardiac image and performing a manual or semi-manual process. Conceptually, the heart can be imaged with multiple slices, similar to the slices of a loaf of bread. The process of calculating EF begins by drawing a contour line around the observed inside wall of a particular heart chamber when it is most full (EDV) so that an outline is obtained of the inside of that chamber (e.g., the left ventricle). The incorporated volume is called the "blood volume." More particularly, the practitioner will take the first two-dimensional image slice of the region of interest, and will draw a contour around the inside perimeter of the selected chamber (essentially drawing a contour line around the area where the blood is contained). The practitioner will then take a next two-dimensional image slice of the same structure and draw a similar contour. This process will continue—usually continuing for about ten (10) image slices for each of the four cardiac chambers while the heart is visibly most full of blood. Thereafter, the same manual or semi-manual process is performed for each slice when the heart is at its smallest state (ESV). The hand-drawn contours applied to multiple slices of the two-dimensional images at end-diastole and end-systole are then used to calculate the EF.

After the drawing process is completed, an estimate can be made with regard to the actual volume of blood (e.g., in milliliters) contained in the particular cardiac structure (e.g. left ventricle) in the EDV and ESV states. These values are themselves important to the practitioner, and a comparison of the two values allows the EF to be calculated. The same process can be used with respect to other cardiovascular structures, such as the right ventricle, and for each of the two atria. However, because of the relative complexity of the contours, it is much easier to perform this analysis with respect to the left ventricle as compared to the right ventricle and the atria. For this reason, it is commonly true that the evaluation described herein is performed only with respect to the left ventricle. This is not because the information derived with respect to the right ventricle and atria are not useful, but instead because of the process of acquiring this information is very time consuming due to the manual nature of drawing the contours. Semi-manual methods using atlas-based methodology have been previously developed, but are frequently inaccurate, even for the left ventricle. Current, semi-manual, atlas-based methods are highly inaccurate for the right ventricle and atria.

SUMMARY

Embodiments concern a system and method for automated machine analysis of medical imaging. A computing system accesses complementary image data of a biological tissue structure (BTS), which image data is stored in a data storage device or in cloud data storage. In some scenarios, the BTS can be a human cardiovascular structure. More particularly, such image data can comprise image data of a cardiovascular structure which has been obtained by using a non-invasive medical image acquisition system. For example, the complementary image data can be data that has been acquired using a medical image acquisition system selected from the group consisting of 2D and 3D echocardiography, magnetic resonance imaging, computed tomography, and/or nuclear medicine scans. The complementary image data is comprised of a plurality of two-dimensional images which represent different views of the BTS respectively aligned with a plurality of distinct image planes.

The plurality of separate convolutional neural networks (CNNs) are used to respectively process each of the plurality of two-dimensional images. As a result of the processing performed by each CNN a probability map is determined for one of the plurality of two-dimensional images. The probability map specifies for each pixel contained therein a probability that the pixel belongs to one of a plurality of pre-defined object classes. Thereafter, the probability maps produced each of the plurality of separate CNNs are adaptively fused into a single output. The output is a segmented output. In the scenario where the BTS is a cardiovascular structure, the segmented output is representative of the cardiovascular structure.

In a scenario wherein the segmented output is representative of a cardiovascular structure, the process can further involve automatically performing a contouring operation to delineate a contour of at least one cardiovascular substructure. Thereafter, the generated contour is used to automatically calculate at least one clinical measurement based on the contour. An example of such a clinical measurement is ejection fraction.

According to one aspect, the plurality of two-dimensional images used for the purposes described herein are respectively aligned with three different imaging planes. For example, the plurality of two-dimensional images can comprise an axial projection, a sagittal projection and a coronal projection.

The adaptively fusing operation described herein involves selectively varying the influence of each probability map as applied to the fusion process in accordance with the degree of reliability accorded to the probability map. According to one aspect, this involves automatically determining the degree of reliability during a training stage of the CNN, without the need for ground truth. More particularly, the degree of reliability during the training stage is automatically determined based on a connected component analysis.

Each of the plurality of CNNs is independently trained using a plurality of two-dimensional training images, where each image respectively corresponds to a predetermined image plane for which the CNN is to be utilized. Fast and reliable convergence of network parameters is achieved during the training and testing by using a modified z-loss type of loss function.

In some scenarios, the plurality of two-dimensional training images are respectively generated by parsing a plurality of image slices from a plurality of three-dimensional image volumes. In this regard, the plurality of two-dimensional training images are selected from one of an axial, sagittal, and a coronal projection. Notably, the plurality of two-dimensional training images can be augmented by using at least one of a translation and angular rotation operation to parse two-dimensional training images, which vary with respect to the axial, sagittal and coronal projections.

The methods disclosed herein are automatically performed by a computing system. The computing system is comprised of at least one electronic processing circuit, which may include a central processing unit (CPU) and/or a graphical processing unit (GPU).

BRIEF DESCRIPTION OF THE DRAWINGS

Embodiments will be described with reference to the following drawing figures, in which like numerals represent like items throughout the figures, and in which.

DETAILED DESCRIPTION

Figure 1:
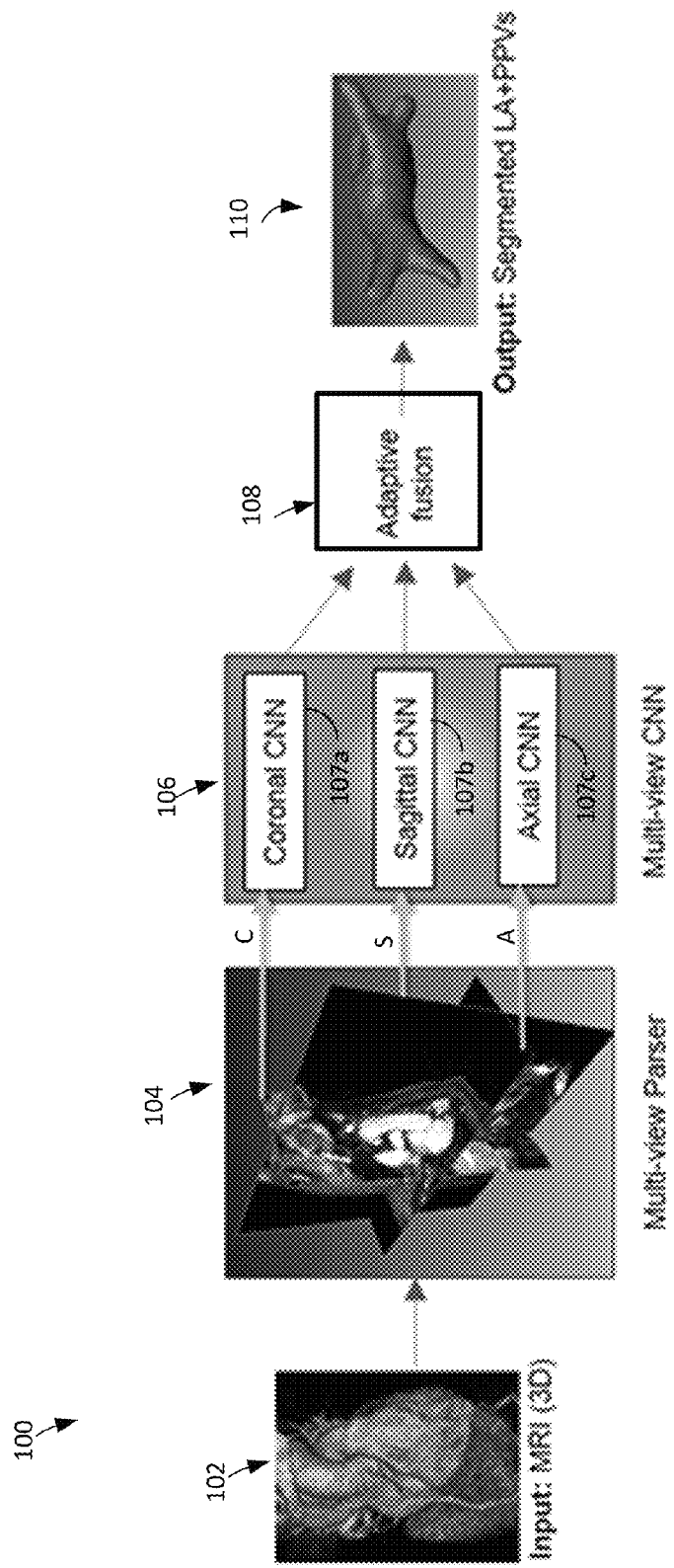
FIG. 1 is a conceptual flow diagram that is useful for understanding a multi-planar convolutional neural network (CNN) disclosed herein.

It will be readily understood that the methods and systems disclosed herein and illustrated in the appended figures could be arranged and designed in a wide variety of different configurations. Thus, the following more detailed description, as represented in the figures, is not intended to limit the scope of the present disclosure, but merely representative of various ways in which the methods and systems can be practiced. Further, while various aspects of the disclosure are presented in the drawings, such drawings are not necessarily drawn to scale unless specifically indicated.

Non-invasive detection of cardiovascular disorders from medical imaging requires quantitative image analysis of the heart and its substructures. There are well-established measurements that physicians, including cardiologists and radiologists, use for disease assessment such as ejection fraction, volume of the four cardiac chambers, and myocardial mass. These measurements are derived as an outcome of precise segmentation of the heart and its substructures.

The usefulness of medical imaging can be enhanced by using computing methods to extract clinically relevant information from images obtained using various modalities such as echocardiography, computed tomography (CT) and magnetic resonance imaging (MRI). Within the medical field, the terms "segmentation" or "mapping" are often used to describe a process by which a given image can be broken down into different meaningful segments which correspond to different tissues or other biologically relevant structures. For example, 3D volume segmentation or mapping can involve extracting 3D objects or structures of interest from volumetric medical images. Because of the innately intricate and variable nature of contours of biological systems, medical image segmentation can be quite challenging for computing algorithms. The process is further complicated by problems such as low contrast, noise, and other imaging ambiguities.

Literature related to cardiovascular image segmentation and providing such measurements into clinical workflow is vast. Among these works, atlas-based methods have been quite popular and favored for many years. Such atlas-based methods involve the use of a large set of 3D image volumes, in which certain areas of interest (e.g. left ventricle) have been delineated by experts. The use of the large dataset allows practitioners to then have a baseline understanding about the expected shape variations of the particular area of interest.

As is known, deep learning involves the use of artificial neural networks (ANNs) for learning tasks. These deep learning techniques can be applied to the task of recognizing and identifying biological structures. For example, deep learning algorithms can be applied to assist with the task of segmenting the heart and its substructures based on medical imaging. Any machine learning process needs to identify features of the structures which are intended for identification. Such deep learning process can be supervised (e.g., where training data is provided in the form of a set of labeled training examples) or unsupervised (where a function is inferred using unlabeled training data).

Deep learning algorithms can avoid expensive and time-consuming engineering which would otherwise be required for such algorithms. In particular, deep learning algorithms capable of learning from "unlabeled" data, can be trained by providing the algorithm with massive amounts of unlabeled data. Of course, unlabeled image data is less informative than labeled image data for supporting the learning process. But if large amounts of unlabeled data are available (e.g., by using image data from a medical database) and assuming a deep learning algorithm can exploit this unlabeled data effectively, then improved performance is potentially possible without the need for massive amounts of time spent with human developed algorithms which then require large amounts of hand-labeled training data.

However, despite all the available methods in the literature, efficiency and accuracy of the results obtained using such deep learning frameworks remains a lingering concern. These concerns are due in part to heavy computational requirements associated with the registration algorithms (e.g., from 13 minutes to 11 hours of computations reported in the literature). Further, the resulting accuracy obtained using conventional methods has not achieved the standards required for clinical medical practice.

One aspect of this disclosure involves a method and system for accurate 3D image segmentation. The disclosed method is based on the use of a multi-planar deep convolutional neural network (CNN) with an adaptive fusion strategy. In particular, the technique involves automatically utilizing complementary image information derived from a three-dimensional image volume, which reveal the cardiovascular structures from different views or angles. This approach has been found to greatly facilitate improved segmentation of cardiovascular structures and function.

A further aspect of the disclosure extends the improved segmentation methods to facilitate multi-object cardiovascular segmentation. Surprisingly, there is very little published research on segmenting all substructures of the cardiovascular system even though clinically established biomarkers heavily rely on shape, volumetric, and tissue characterization of these cardiovascular substructures. The methods and systems disclosed herein fill this void from a machine learning perspective. The disclosed embodiments facilitate automatic delineation of up to seven substructures of the cardiovascular system from a variety of different commonly used medical imaging modalities. The seven substructures include: left atrium (LA), left ventricle (LV), right atrium (RA), right ventricle (RV), myocardium of left ventricle (Myo), pulmonary veins (PVs), aortic root and aorta (Ao), and pulmonary arteries (PAs).

A further advantage of the disclosed embodiments is that they can be used for a variety of different commonly used medical imaging modalities such as 2D and 3D echocardiography, magnetic resonance imaging, computed tomography, and/or nuclear medicine scans. Two-dimensional echocardiography is commonly used to diagnose cardiovascular disease but has known limitations with regard to accuracy of cardiac volumes and ejection fraction. These limitations derive from the subjective nature of hand-drawn contours or visual estimation currently used for cardiovascular chamber segmentation with this modality. Cardiovascular CT and MRI are popular in non-invasive assessment of cardiovascular diseases (CVDs) with significantly improved accuracy compared with 2D echo. CT is more often used compared to MRI due to its fast acquisition and lower cost. On the other hand, MRI has excellent soft tissue contrast, no ionizing radiation, and is considered to be the gold standard for cardiac chamber quantification and vascular mapping. Extensive research and clinical applications have shown that both CT and MRI have a vital role in assessment of CVDs. However, available image analysis methods have been either tuned for CT or MRI only. The disclosed CNN herein works well with all such imaging modalities.

Accordingly, the present disclosure concerns architectural designs of deep learning networks which solve multi-label and multi-modality image segmentation challenges, for efficient use in the clinical setting with limited computing power.

The solutions disclosed herein are primarily presented with respect to segmentation and contouring of cardiovascular structures. The focus is on cardiovascular structures to facilitate understanding and provide a concrete example of one way in which the solution can be applied to a particular biological structure. However, it is understood that the solution is not limited to cardiovascular structures. Instead, the cardiovascular structures merely represent one type of biological tissue structure (BTS) in which the segmentation, contouring and automated methods disclosed herein can be applied for advancing clinical measurements and analysis. It will be readily appreciated that the systems and techniques presented herein can be applied to many other types of BTS for a wide variety of clinical purposes.

The methodology disclosed herein differs in several important respects as compared to the prior art. In general, large volumes or images are required to "train" a deep learning algorithm as described herein. Training involves providing a large dataset to the deep learning software and allowing the program to teach itself how to perform a function. But this training requirement presents a problem for development purposes due to an insufficient number of available cardiovascular images and limitations with large amounts of computer memory needed to perform this training from scratch. Accordingly, a different approach is adopted herein whereby complex datasets are parsed into two-dimensional components (axial (A), sagittal (S), and coronal (C)). Thereafter, a separate deep learning CNN architecture is utilized for each 2D component.

The results obtained from the three separate CNN networks are combined through the use of a novel adaptive fusion mechanism. The adaptive fusion mechanism allows complementary information of each CNN to be utilized to improve segmentation results. The adaptive fusion mechanism is based on a new strategy called "robust region," which measures (roughly) the reliability of segmentation results without the need for ground truth. This strategy is disclosed below in further detail.

Further, the process has been optimized by means utilizing a new loss function in the proposed network, based on a modified z-loss. The rationale behind the choice of z-loss as a loss function is the following: the z-loss function provides an efficient training performance as it belongs to spherical loss family, and it is invariant to scale and shift changes in the output. Consequently, extreme, deviant output parameters are advantageously avoided. In testing stage, this loss function provides faster convergence too for network parameters as compared to conventional methods. This improved segmentation results due to fast and reliable allocation of network parameters, but also provides a significant acceleration of the segmentation process. With the embodiments disclosed herein, the overall segmentation process in testing stage for a given 3D cardiovascular MRI requires at most 10 seconds in a single GPU, and 7.5 minutes in CPU on a conventional workstation.

Multi-Object Multi-Planar Convolutional Neural Network (CNN)

The solution disclosed herein is called Multi-Object Multi-Planar Convolutional Neural Network (CNN). Overall, the proposed system takes cardiovascular scans from one or more modalities as an input and parses them to three perpendicular planes: Axial (A), Sagittal (S), and Coronal (C). For each plane (and modality), a 2D CNN is trained to label pixels. After training each of the 2D CNNs separately, a novel adaptive fusion strategy is utilized by combining the probability maps of each of the CNNs. The details are explained in the following.

A process for deep learning based segmentation of cardiovascular substructures is summarized in FIG. 1. As an example, the process can be used for segmentation of the left atrium (LA) and pulmonary veins (PPVs). However, as will be appreciated, the basic process can be applied to other tissue structures, including other cardiovascular structures. The basic process can be extended to multiple imaging modalities and complex, multi-object structures. These and other details will be explained in detail below.

Referring to FIG. 1, a deep learning process 100 can begin at 102 by obtaining a 3D image volume of the cardiovascular structures (LA and PPVs in this example), utilizing a suitable imaging technology such as CT or MRI. In this example, we assume the input is a 3D MRI image volume. A similar process can be applied using axial, sagittal and coronal images originally obtained from a 2D data set. At 604, the 3D volume data is parsed into 2D image components comprising axial image A, sagittal image S, and coronal image C. Parsers capable of extracting the axial image, sagittal image and coronal image from a 3D image volume are well known in the art and therefore will not be described in detail. However, any software library or widget capable of performing the image parsing function can be used for this purpose.

At 106 the 2D image thus obtained for each plane in 104 is respectively communicated to a corresponding CNN 107a, 107b, 107c. In an embodiment disclosed herein, the same CNN architecture is advantageously used at 107a, 107b, 107c for processing the views corresponding to each of the axial image A, sagittal image S, and coronal image C. This approach of extracting the 2D images from the 3D image volume is advantageous considering limitations of computer memory and 3D data. More particularly, by initially separating the problem into three 2D processing problems, we reduce the computational burden of the CNN training by constraining the problem into a 2-dimensional domain.

Each CNN 107a, 107b, 107c processes one of the corresponding parsed 2D images to obtain a pixel-wise segmentation of the cardiovascular structures. The resulting pixel-wise segmentation from each CNN 107a, 107b, 107c is subsequently combined at 108 by means of a novel adaptive fusion strategy. The fusion operation at 108 is designed to maximize the information content from different views to finally produce the segmented cardiovascular structure at 110. A similar approach can be used for multimodality imaging methods and multi-object cardiovascular segmentation, including multilayered segmentation of 2D imaging datasets (e.g., 2D MRI or 2D echocardiography). The details of various steps associated with the processing are described below in greater detail.

By convention, each imaging plane (axial, sagittal, or coronal) includes slices in a specified order. The same pixel has its corresponding pixel in the other planes. There are three output maps which are produced, one corresponding to each CNN's output. At the final step, these three output maps (which are probability maps) are combined to deliver only one output. This result is achieved by assessing the same pixel's three outputs as produced by the three CNNs. The final step involves determining the final single probability value for that one pixel based on the three probability values resulting from the three respective assessments in the different planes. This final determining step is performed by means of a fusion operation which involves unequal weighting of each plane's output. Unequal weights are learned in the training stage and are affected by the resolution of that specific plane. For instance, sagittal plane may get lower weight on the final output due to lower resolution while coronal and axial may get higher weights due to their better in-plane resolution.

Encoder-Decoder for Multi-Planar CNN

The methods and systems disclosed herein make use of an encoder-decoder CNN architecture, similar to that described in Noh, et al. "Learning deconvolution network for semantic segmentation," in Proceedings of the IEEE International Conference on Computer Vision, 2015, pp. 1520-1528. The approach utilized in Noh is known in the art and therefore will not be described here in detail. However, a brief explanation is provided here to facilitate understanding of the various embodiments.

Figure 2:
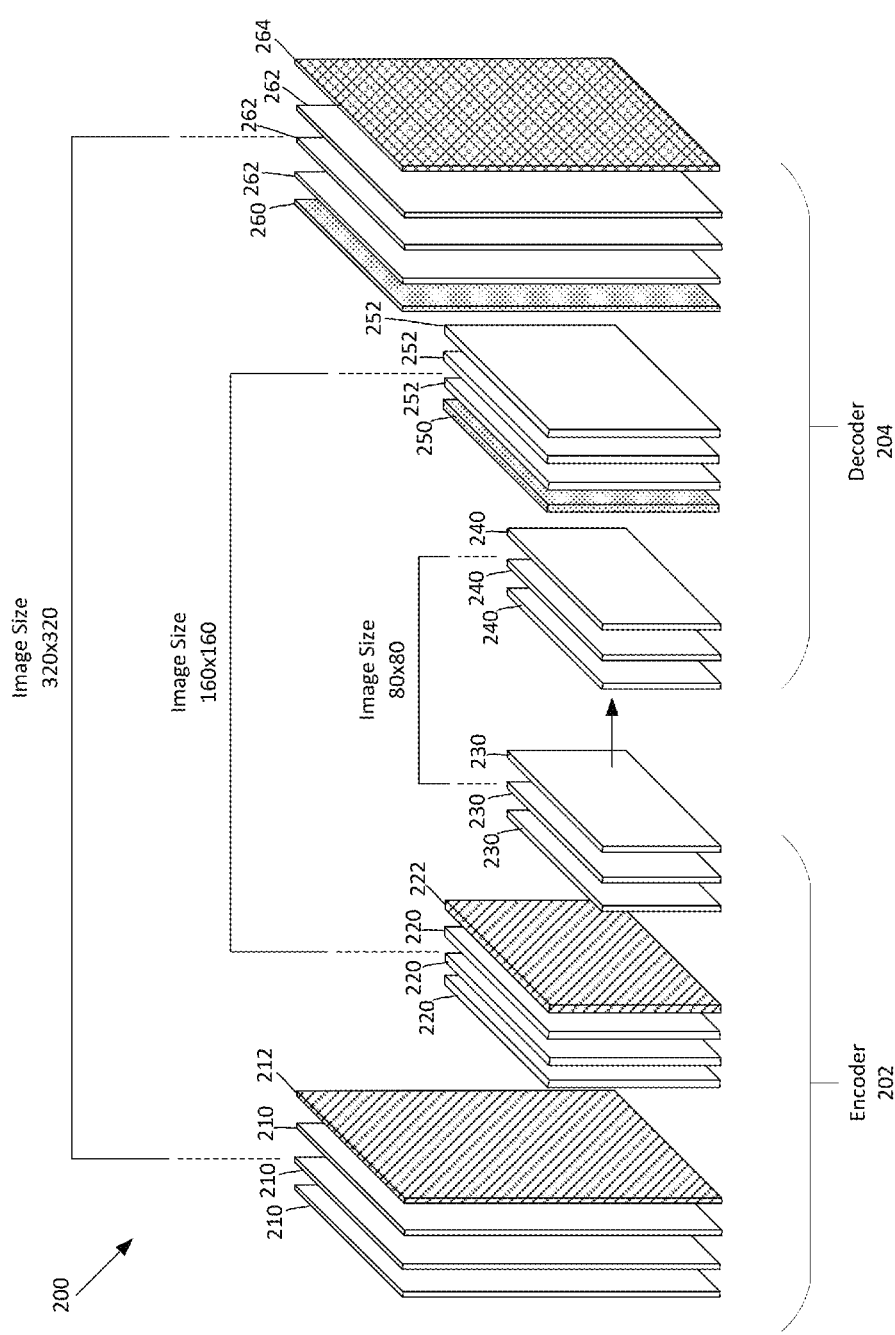
FIG. 2 is a drawing that is useful for understanding an architecture of a CNN which can be used for segmenting a cardiovascular structure.

Referring now to FIG. 2, there is illustrated an exemplary CNN 200 that can be used for object segmentation in the cardiovascular setting. For example, the CNN 200 can be used for segmenting the LA and PPVs in cardiovascular imaging. The CNN 200 is representative of one of the coronal CNN 107a, sagittal CNN 107b, or the axial CNN 107c. Since the architecture of each of these CNNs can be the same, only a single network 200 is shown in FIG. 2.

The network 200 is comprised of two main parts, namely an encoder portion 202 and a decoder portion 204. The encoder portion 200 receives a 2D input image comprised of a plurality of pixels. For example, the input image can comprise one of an axial image, sagittal image and coronal image obtained from the 3D image volume or from a 2D dataset. As explained below, the encoder portion 202 is configured to perform feature extraction operations which are intended to transform the input image to a multi-dimensional feature representation.

The encoder portion 202 will comprise a plurality of layers including convolutional layers 210, 220, 230 and pooling layers 212, 222. As explained below in greater detail, each of the convolutional layers 210, 220, 230 is actually comprised of a series of sub-layer operations (not shown), which, respectively, perform the convolution operation, followed by batch normalization, and finally rectified linear unit (ReLU) operations. To avoid confusion in the drawing, the batch normalization and ReLU layers are not expressly shown. Each of the different types of processing operations described herein are well known in the art and therefore will not be described here in detail. However, a brief discussion of each is provided to facilitate understanding of the disclosure.

Within the encoder, each of the convolutional layers 210, 220, 230 will perform a convolution operation on the input image, passing the result to the next layer. The convolution operation performed in such layers is well known and therefore will not be described here in detail. However, it should be appreciated that a primary purpose of such convolution operation is to extract features from the input image. As is known, each such convolution operation reduces the number of free parameters and improves generalization. A matrix having n×n dimension is used for the convolution operation. This matrix is commonly referred to as a filter, a kernel or a feature detector. There are 64 filters for each of the convolution layers 210. There are 128 filters for each of the convolution layers 220. There are 256 filters for each of the filter layers 230. A resulting matrix output from the convolution operation in each layer is produced by sliding the filter over the image and computing the dot product. This output matrix is sometimes referred to as an activation map or a feature map.

A batch normalization operation is included for each convolutional layer 210, 220, 230. As is known, the function of the batch normalization operation is performed to reduce the internal-covariate-shift problem which is common to deep neural networks. The batch normalization operation is well known in the art and reduces the internal-covariate-shift by normalizing input distributions of every layer to the standard Gaussian distribution.

An ReLU operation is also provided to each convolution layer. The ReLU process comprises an operation applied on each element or pixel of an input. The process replaces all negative pixel values in a feature map by a zero value. This process is used to intentionally introduce non-linearity into the CNN since most of real-world data representing cardiovascular structures would be non-linear. In this regard it will be appreciated that the convolution processing is comprised of element wise matrix multiplication and addition. As such, the convolution layers comprise linear operations. Non-linearity is accounted for in the CNN by introducing a ReLU, which is understood to be a non-linear function. Of course, other non-linear functions can be used for this purpose but experience has shown that better performance is generally obtained using ReLU.

Pooling operations are performed in layers 212, 222 between some of the convolution layers in FIG. 2, as shown. Pooling layers are well known in the art and therefore will not be described here in detail. However, it should be appreciated that the pooling layers 212, 222 allow a larger image to be described more simply by aggregating statistics of convolved features to make the input representations smaller and more manageable from a computational perspective. For example, in some scenarios described herein the pooling operations involve determining the maximum value of a particular feature over all elements within a region of the 2D input, and assigning that max value to the entire region. Such a process is commonly known as "max pooling." An advantage of such pooling operations is that they can filter out noise in lower layers (e.g. small transformations, distortions and distortions) by abstracting a group of activations in a particular region to comprise a single representative value. This process can help with subsequent classification steps by ensuring that only robust activations remain in the upper layers of the process. In the scenario shown in FIG. 2, each of the pooling layers 212, 222 reduce the image dimensions by half.

The decoder portion 204 basically comprises a shape generator. The shape generator performs an object segmentation function based on the features which are extracted in the encoding network. As shown in FIG. 2, the decoder portion 204 will advantageously mirror the architecture of the encoder portion 202. As such, the decoder portion 204 will comprise a plurality of layers which include un-pooling layers 250, 260. The un-pooling layers 250, 260 each perform an up-sampling function to convert the images back to original size. The deconvolution layers 252, 262 comprise deconvolution, batch normalization and ReLU operations. The resulting output of the decoder portion 204 comprises a probability map. The probability map specifies for each pixel in the original image the probability that such pixel belongs to one of a plurality of pre-defined classes.

In the decoder portion 204, the up-sampling (bilinear interpolation) performed by the un-pooling layers 250, 260 produces an enlarged activation map which is sparsely populated. The filters used in the deconvolution layers are generated by means of the training process and are used to reconstruct the shape of an input object. Filtering performed at the lower level layers (e.g. layers 240) is used to generate the basic shape of objects in the image. Increasingly finer levels of object detail are extracted by learned filters in the higher levels (e.g. layers 262) as the image is propagated through the decoder.

In total, the exemplary network 200 disclosed herein includes 23 layers (11 in the encoder, and 12 in the decoder unit). Accordingly, the entire network can be quite deep. Two max-pooling layers 212, 222 in the encoder unit 202, respectively, reduce the image dimensions by half. A total of 19 convolutional layers are used, including 9 convolutional layers in the encoder, and 10 de-convolutional layers in the decoder. Correspondingly, there are at total of 18 batch normalization layers, and 18 ReLU layers used in the encoder/decoder sections. Specific to the decoder unit 204, two up-sampling or un-pooling layers 240, 260 are used to convert the images back into original sizes. The kernel size of all filters in the scenario describe herein are considered as 3×3. The number of filters in the last convolution layer 264 is equal to the number of classes of objects which are to be segmented. In the basic embodiment shown in FIG. 2, only a single object is to be segmented (e.g., left ventricle only). Accordingly, only a single filter is needed at this stage.

The final convolution layer 264 is followed by an operation comprising a softmax function. The well-known softmax function is sometimes referred to as a normalized exponential function. The softmax function generates a probability score for each pixel. The resulting probability map for each pixel is then output to the adaptive fusion block 108.

It will be appreciated in FIG. 2 that the image size is not necessarily fixed for the CNN for each plane of imaging. In other words, image size can vary from one plane relative to the other planes. Also, the exact image size is not critical and the values shown are merely intended as one possible example.

Multi-Planar Adaptive Fusion

After training each 2D CNN separately 107a, 107b, 107c, a proprietary adaptive fusion process is used to combine the probability maps of each of the CNNs to form the final 3D volume. Since cardiovascular MRI is often not reconstructed with isotropic resolution, varying degrees of segmentation accuracy were expected with regard to different planes of imaging. Isotropic resolution refers to images made up of voxels with all sides that are equivalent in length that allows for identical resolution in all dimensions.

To alleviate potential adverse effects caused by non-isotropic resolution of a particular view, an adaptive fusion strategy is used. For a given MR volume I, and its corresponding segmentation o, a new strategy is used, called "robust region." With this approach, the reliability of the output segmentation o is roughly determined by assessing its object distribution. To achieve this, we hypothesized that the output should include only one connected object when the segmentation was successful. Accordingly, if the output included more than a single connected object, then these were considered to be false positives. Connected objects for this purpose may be understood to be comprised of clusters or blobs of pixels with the same value such that they are not separated by a boundary.

By evaluating the extent of these false positives, and using this factor as a metric of quality, respective performance of segmentation operations in A, S, and C views can be compared and weighted. To this end, a connected component analysis (CCA) is advantageously used to rank output segmentations. Various methods for CCA are well known in the art and therefore will not be described in detail. Briefly, these CCA methods (which are sometimes called connected-component labeling or blob extraction) utilize an algorithm to detect connected regions in the 2D pixel map. The process is usually performed on a binary image obtained as a result of a thresholding step.

Figure 3:
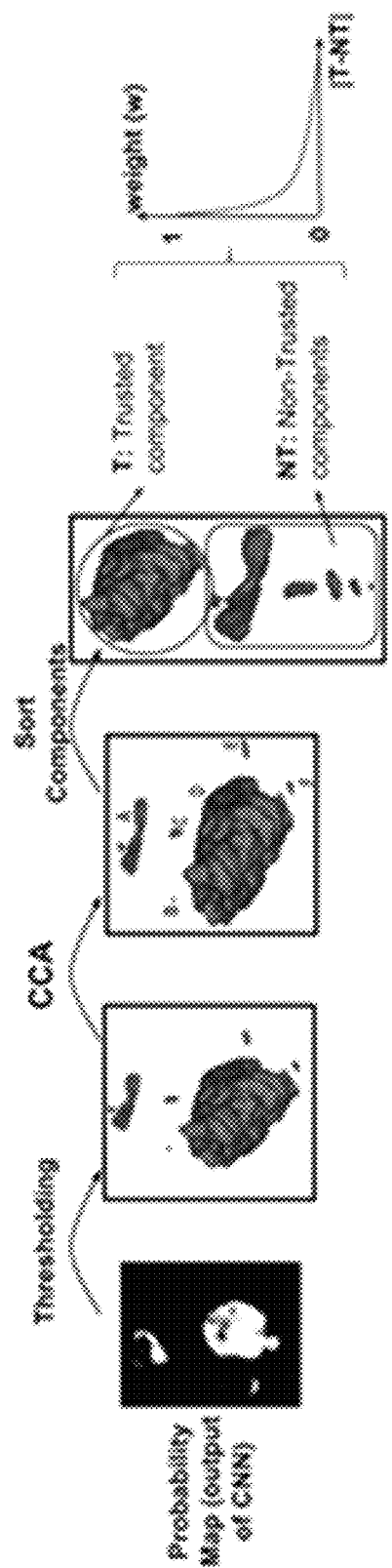
FIG. 3 is a drawing which is useful for understanding a weighting scheme used during a training process for adaptive fusion of information from a plurality of image planes.

The foregoing concept is illustrated in FIG. 3, which shows that the output of a CNN can be thresholded and then subjected to CCA. The output of a CNN disclosed herein represents a probability map showing the object and background probabilities. Often 0.5 is used for thresholding the probability map and for obtaining the object of interest. Since it is expected that some false positive findings will appear in the images, we develop a strategy to find those false positives to remove from the final output. This strategy is called trusted and non-trusted region identification. As seen in FIG. 3, resulting objects are ranked based on their size using connected component analysis (CCA), and sorted components are classified as trusted and non-trusted regions. Based on supervised observations, a trusted component is expected to have the largest component in the output results, and the rest should be untrusted objects due to their small size. Note also that these small objects are not connected to main (bigger) object, therefore they are considered as false positive. Only the trusted component is considered in the final evaluation. A simple calculation is devised for this purpose as follows. The trusted region's volume is denoted by T, and non-trusted components volume is considered as NT. T-NT is considered as a goodness metric for purposes of evaluating the output of a particular CNN. If this metric is a small value, then it may be understood that there are many false positives in the output of the particular CNN. T-NT, in other words, shows strength for fusion with the other views.

In the adaptive fusion process disclosed herein, these rankings of output segmentations obtained from CCA were used to selectively vary the contribution weighting of a particular CNN for a particular view. More particularly, the contribution of a particular CNN was reduced when false positive findings (non-trusted objects/components) were large and true positive findings (trusted object/component) were small.

The adaptive fusion strategy can be described as $$CCA(o) = \{o1, \ldots, on | \cup oi = o, \text{ and } \cap oi = \phi\}.$$

where o denotes output of the network, $\phi$ means empty set, and i indicates components of the output o based on CCA analysis. The contribution of the CNN for each plane of imaging was computed based on a weighting $$w = \max_i \{|oi|\}/i|oi|$$

where w is a weighting factor proportional to largest component's volume to the entire volume of the output. The foregoing weighting definition shows that higher weights are assigned to the component with the largest volume dominating the output volume. In other words, if T-NT is large for a given view, then the weight (w) is large. Note that this block was only used during the test phase, and not during the training phase.

Training Process

Training of the CNN described herein involves using cardiovascular images along with corresponding expert annotated ground truth (also called surrogate truth). The images were used to train each CNN after the images were parsed into three views (axial, sagittal, and coronal-A, S, and C). For 3D datasets, 3D images were parsed into A, S, and C views, and the resulting 2D images were then available to train the CNN. To provide enough training images for the networks, data augmentation was applied to training images by rotation and zoom in. In other words, slightly different training images were obtained from the same 3D image volume by changing the rotation angle slightly and/or changing the zoom in. These different training images were then treated as separate independent training images. For instance, by using translation and rotation only as data augmentation, it is possible to obtain 60K images from only 20 cardiac MRIs. In the current embodiment, data augmentation is used to A, S and C slices independently because there are three networks to train them.

As a preprocessing step, all images underwent anisotropic smoothing filtering and histogram matching. These operations will remove some of the unnecessary difficulties/ challenges prior to learning algorithms.

Loss Function

Data loss in the context of supervised learning of a CNN is understood to be a measure of the compatibility between a prediction (e.g. the class scores in classification) and the ground truth label. As such, a loss function is conventionally used to measure the quality of a particular set of parameters based on how well the induced scores agree with the ground truth labels of the training data. To facilitate the training process in the disclosed embodiments, we used a new loss function (called modified z-loss) that can facilitate estimation of the parameters of the proposed network at a much faster rate.

In particular, we trained end-to-end mapping with the loss function:

$$L(o,c) = \text{softplus}(a(b-zc))/a, \text{ called } z\text{-loss, where}$$

o denotes output of the network, c denotes the ground truth label, and zc indicates z-normalized label, obtained as $zc = (oc - \mu)/\sigma$, where mean ($\mu$) and standard deviation $\sigma$ are obtained from o.

The z-loss function is known in the art. For example, this function is described in Alexandre de Br'ebisson and Pascal Vincent, "The z-loss: a shift and scale invariant classification loss belonging to the spherical family," arXiv preprint arXiv:1604.08859, 2016. However, it should be understood that z-loss is simply obtained with the re-parametrization of the well-known soft-plus (SP) function (i.e., SP (x)=ln(1+ ex)) through two hyper-parameters: a and b. These two hyper-parameters are learned during the training process by changing their values in multiple different settings. In the disclosed embodiments, these hyper-parameters can be fixed, and the network can thereby be trained with a reduced z-loss function. The z-loss function provides an efficient training performance as it belongs to the spherical loss family; and it is invariant to scale and shift changes in output. Consequently, extreme, deviant output parameters are advantageously avoided.

Multi-Object Cardiovascular Segmentation

The basic methods and systems described above can be extended to facilitate multi-object cardiovascular segmentation. For example, these methods and systems can facilitate an accurate image segmentation algorithm that automatically delineates seven substructures of the cardiovascular system from commonly used medical imaging modalities such as echocardiography, magnetic resonance imaging, computed tomography, and/or nuclear medicine scans.

The multi-object (MO) segmentation disclosed herein can be trained from scratch for voxel-wise labeling of the following structures: myocardium of left ventricle (Myo), left atrium (LA), left ventricle (LV), right atrium (RA), right ventricle (RV), pulmonary veins (PPVs), aortic root and aorta (Ao), and pulmonary arteries (PAs). Notably, the method has been evaluated with 4-fold-cross-validation based on the multi-modality whole heart segmentation challenge (MM-WHS 2017) dataset. Precision and dice index values of 0.93 and 0.90, and 0.87 and 0.85 were achieved for CT and MR images, respectively. The whole heart segmentation time from a CT volume was about 50 seconds, with MRI assessment performed in about 17 seconds.

Figure 4:
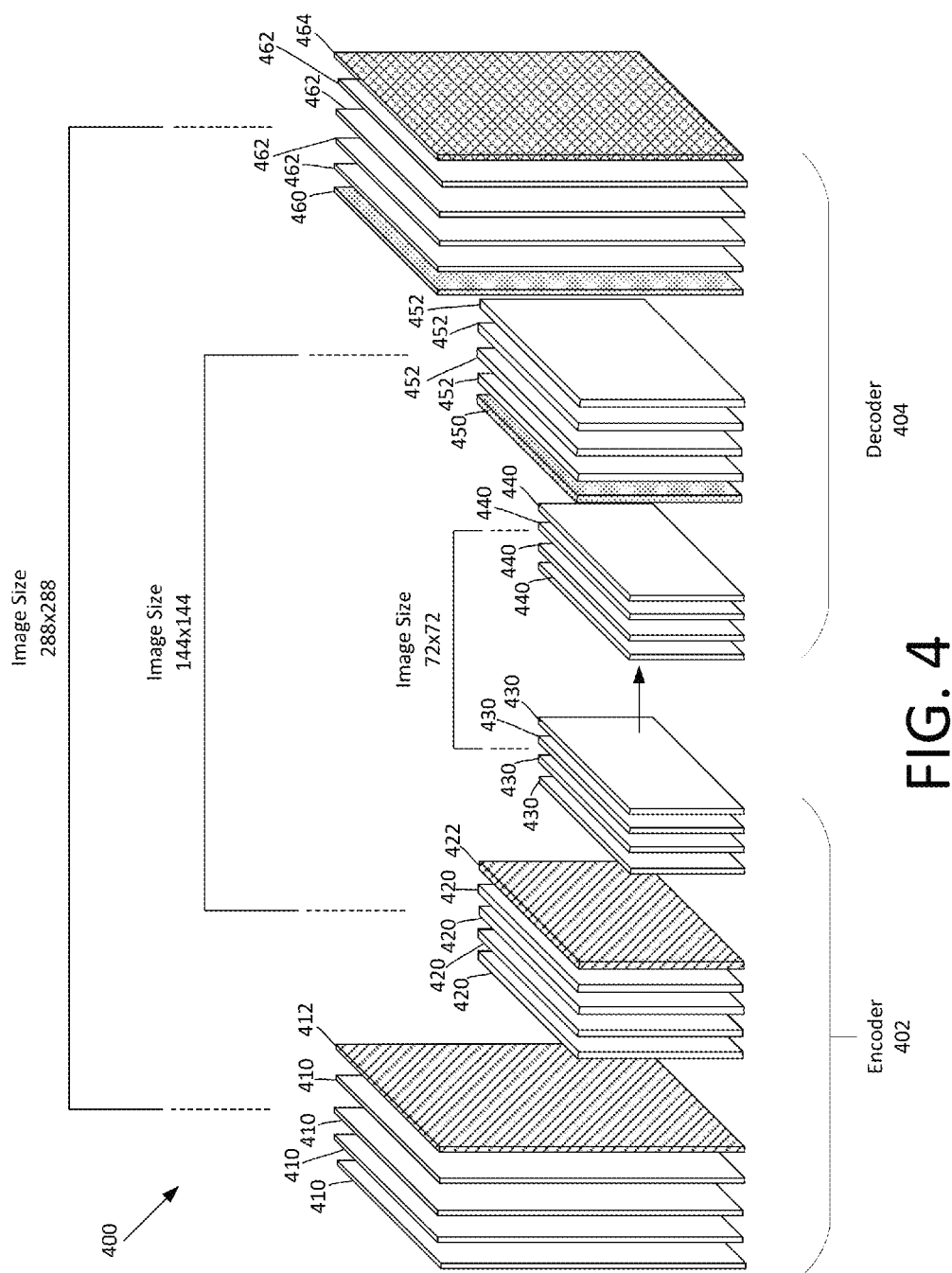
FIG. 4 is a drawing that is useful for understanding an architecture of a CNN which can be used for multi-object segmentation of a plurality of cardiovascular structures.

Referring now to FIG. 4 there is shown a CNN architecture 400 for multi-object cardiac segmentation. The CNN architecture shown in FIG. 4 is similar to that which is shown in FIG. 2 but includes additional convolution layers. This slight change does not affect the overall network structure. Depending on the amount of GPU computing power which is available, additional convolutional layers can also be added. In FIG. 2, the CNN 400 would be representative of one of the coronal CNN 107a, sagittal CNN 107b, or the Axial CNN 107c as applied to a multi-object segmentation scheme.

The network 400 is comprised of encoder portion 402 and decoder portion 404. The encoder portion 402 includes convolutional layers 410, 420, 430 and pooling layers 412, 422. Each of the convolutional layers 410, 420, 430 actually comprises three sub-layers including a convolution operation, followed by a batch normalization operation, and finally an ReLU operations as described above. In the CNN 400, there are 64 filters for each of the convolution layers 410. There are 128 filters for each of the convolution layers 420. There are 256 filters for each of the filter layers 430. Pooling operations are performed in layers 412, 422 between some of the convolution layers in FIG. 4, as shown. The pooling layers can comprise max-pooling operations which reduce the image dimensions by half.

The decoder portion 404 will comprise a plurality of deconvolution layers 452, 462 and un-pooling layers 450, 460. The deconvolution layers 452, 462 actually comprise a plurality of sub-layers dedicated to performing deconvolution operations, followed by batch normalization and finally ReLU operations. To avoid confusing the drawing, these individual sub-layers are not shown in FIG. 4. The un-pooling layers 450, 460 perform up-sampling (e.g., bilinear interpolation) to convert the images back to original size. As such, these un-pooling layers can also be referred to as up-sampling layers.

The resulting output of the decoder portion 404 comprises a probability map which specifies for each pixel the probability that such pixel belongs to one of a plurality of pre-defined classes. As with decoder portion 204, the filters used in the deconvolution layers 404 are generated by means of the training process and are used to reconstruct the shape of an input object.

In total, the exemplary network 400 disclosed includes 29 layers (14 in the encoder portion, and 15 in the decoder portion). A total of 25 convolutional layers are used, including 12 convolutional layers in the encoder, and 13 deconvolutional layers in the decoder. Each convolution layer (except for layer 464) is comprised of a convolution operation, a batch normalization operation, and an ReLU operation. Specific to the decoder unit 204, two up-sampling or un-pooling layers 440, 460 are used to convert the images back into original sizes. The kernel size of all filters in the scenario describe herein are considered as 3×3. The number of filters in the last deconvolution layer 464 is equal to the number of classes of objects which are to be segmented. For the multi-object segmentation, process described, 8 filters can be used (for 7 objects and background). This final deconvolution layer 464 is followed by a softmax operation (which is not expressly shown as a separate layer in FIG. 4, but is assumed to be part of the deconvolution layer). The softmax function generates a probability score for each pixel so that a probability map is then output from the CNN to the adaptive fusion block 108. Training of the multi-modal multi-object CNN 400 is performed in a manner similar to that described herein with respect to CNN 400.

Multi-Object Adaptive Fusion

Multi-object adaptive fusion is similar to the multi-planar adaptive fusion process described above. To facilitate understanding of the process, let I and P denote an input and output image pair, where the output is the probability map of the CNN. Also, let the final segmentation be denoted as o. In a manner similar to that shown in FIG. 3, o is obtained from the probability map P by taking the maximum probability of each pixel in all classes (labels). Thereafter, a connected component analysis (CCA) is applied to o to select reliable and unreliable regions in the same manner as described with respect to FIG. 3, where unreliable regions are considered to come from false positive findings. Although this approach only gives a "rough" estimate of the object, the information can be used advantageously for assessing the quality of segmentation from different planes.

If it is assumed that n is the number of classes (structures) in the images and m is the number of components in each class, then connected component analysis can be performed as follows:

$$CCA(o)=\{o_{11}, \quad . \quad . \quad . \quad ,o_{nm}|\cup o_{ij}=o,$$
$$\text{and } o_{11}, \ldots, o_{nm}|\cap o_{ij}=\phi\}.$$

For each class n, we assign reliability parameters (weights) to increase the influence of imaging planes that have more reliable (trusted) segmentation as follows:

$$w=^P_i\{\max_j\{|o_j|\}\}/^P_{ij}|o_{ij}|, \text{ where}$$

w indicates a weight parameter, o indicates object, and i and j class of object and its component, respectively.

Figure 5:
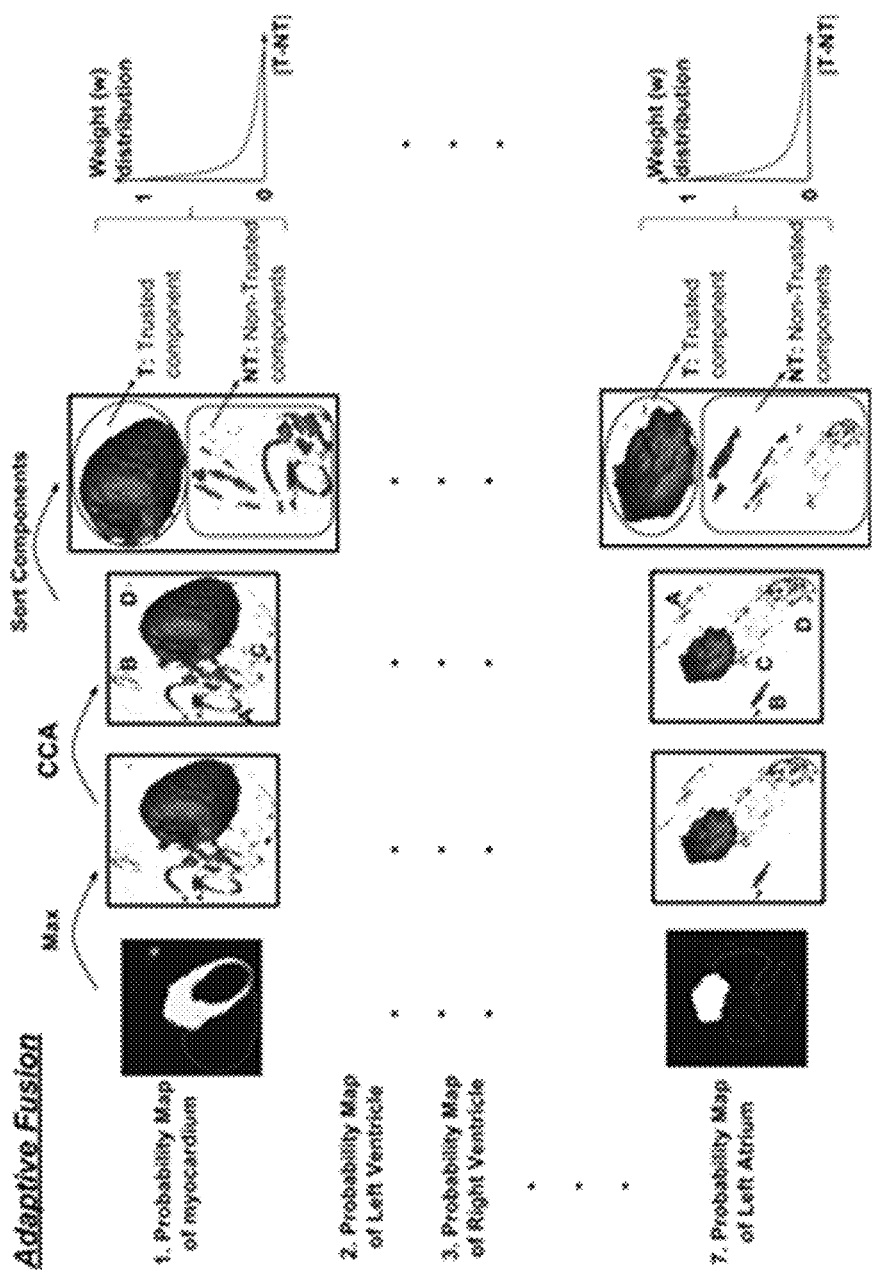
FIG. 5 is drawing which is useful for understanding a weighting scheme used during a training process for multi-object adaptive fusion of information obtained from a plurality of image planes.

This concept is illustrated in FIG. 5 which shows that a separate weight parameter can be calculated for each object class n. For example as separate weight parameter can be calculated for myocardium of left ventricle (Myo), left atrium (LA), left ventricle (LV), right atrium (RA), right ventricle (RV), pulmonary veins (PPVs), aortic root and aorta (Ao), and pulmonary arteries (PAs).

With the foregoing weighting parameter, higher weights are assigned to the component in the image with the largest volume dominating the output volume, as similar to the concept introduced above. In our interpretation of the CCA, the difference between trusted and non-trusted regions are used to guide the reliability of the segmentation process: the higher the difference, the more reliable the segmentation.

During the test phase, we simply use the predetermined weights obtained during the training stage.

Multi-Modality Adaptive Fusion

A variety of different medical imaging modalities can be used for assessment of cardiovascular diseases (CVDs). Examples of such imaging modalities include 2D and 3D echocardiography, magnetic resonance imaging, computed tomography, and/or nuclear medicine scans. Further, extensive research and clinical applications have shown that both CT and MRI have a vital role in assessment of CVDs. However, conventional image analysis methods have been either tuned for CT or MRI only. In contrast, the methods and systems disclosed herein have been demonstrated to provide excellent segmentation results for a variety of different imaging modalities, including but not limited to CT and MRI.

There is a consensus that multi-modality imaging and image analysis improves efficacy of cardiovascular disease diagnosis, interventions, and clinical outcome. Morphology and functional information can be obtained from separate (complementary) imaging modalities and fused to enhance clinical decision making. This requires an algorithm that adaptively fuses cardiovascular imaging modalities.

The methods and systems disclosed herein provide a framework for accurately segmenting all cardiovascular structures from multiple imaging modalities with high efficiency and accuracy. To facilitate this ability, we train multiple CNNs from scratch for different image planes, and then facilitate an adaptive fusion strategy for information maximization for pixel labeling. The result is a system that can provide accurate segmentation results despite limited data and hardware support. As such the methods disclosed herein can provide an efficient tool to delineate cardiovascular structures with high precision, accuracy, and efficiency. These methods can also be employed in segmentation of other cardiovascular structures including the branch pulmonary arteries, aortic root, ascending aorta, descending aorta, aortic branch vessels including the extra- and intracranial vessels, vessels of the arms and legs, the abdominal aorta and its branches (celiac artery, hepatic artery, splenic artery, renal arteries and mesenteric vessels), iliofemoral vessels. Notably, the benefits of this approach are not limited to cardiac structures, but can be extended to other tissues. For example, these methods can be used to efficiently segment the venous structures of the body including the superior vena cava (SVC), inferior vena cava (IVC), iliofemoral veins, extra- and intracranial venous structures, portal venous systems including the superior mesenteric vein and splenic vein, hepatic veins, and veins of the extremities.

In a scenario disclosed herein the CNN architecture according to FIGS. 1-6 is used to delineate the contours of various different cardiovascular structures. Once these contours are clearly established or delineated using the disclosed methods, the system can perform one or more operations to automatically facilitate certain measurements that physicians use for cardiac disease assessment such as ejection fraction, volume of the four chambers, and myocardial mass. These measurements are derived as an outcome of precise segmentation of the cardiovascular system. Various techniques for arriving at such measurements are well known by physicians but can be very time consuming. However, by using the precise segmentation methods described herein, the methods can be automated for greater accuracy and efficiency.

Once segmentation results are obtained for each heart substructure, volumetric measures (such as volume of chambers) will be extracted. Thereafter, ejection fraction will be calculated from the ventricular volumes at end-diastole and end-systole. Note that the framework presented herein can be used for additional cardiovascular measurements once all the structures are outlined (contoured) as a result of the segmentation. For instance, myocardial mass can be defined and compared with the myocardial mass on prior imaging studies.

Exemplary Hardware Implementations

The methods disclosed herein can be realized in one computer system. Alternative embodiments can be realized in several interconnected computer systems. Any kind of computer system or other apparatus adapted for carrying out the methods described herein is suited. A typical combination of hardware and software can be a general-purpose computer system. The general-purpose computer system can have a computer program that can control the computer system such that it carries out the processing described herein. A computer system as referenced herein can comprise various types of computing systems and devices, including a server computer, a personal computer (PC), a laptop computer, a desktop computer, a workstation or any other device capable of executing a set of instructions (sequential or otherwise) that specifies actions to be taken by that device.

Figure 6:
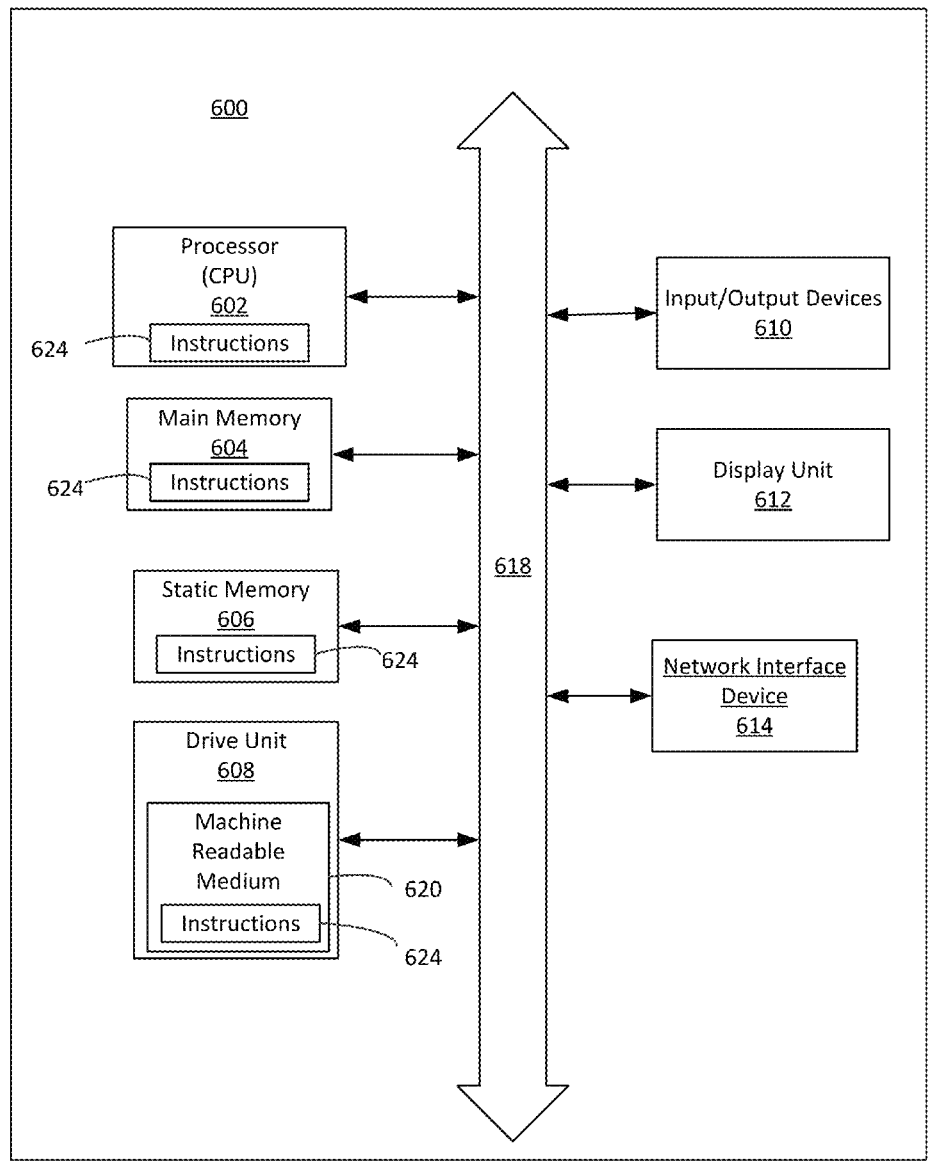
FIG. 6 is a block diagram of an exemplary computer system that can perform processing operations as described herein for purposes of implementing an overlay network.

The computer system(s) described herein can comprise one or more components such as a computer processor, an application specific circuit, a programmable logic device, a digital signal processor, or other circuit programmed to perform the functions described herein. Referring now to FIG. 6, there is shown a hardware block diagram comprising an exemplary computer system 600. The machine can include a set of instructions which are used to cause the computer system to perform any one or more of the methodologies discussed herein. In a networked deployment, the machine can function as a server.

In some embodiments, the computer 600 can operate independently as a standalone device. However, embodiments are not limited in this regard and in other scenarios the computer system can be operatively connected (networked) to other machines in a distributed environment to facilitate certain operations described herein. Accordingly, while only a single machine is illustrated it should be understood that embodiments can be taken to involve any collection of machines that individually or jointly execute one or more sets of instructions as described herein. These embodiments include cloud-based networking and computing.

The computer system 600 is comprised of a processor 602 (e.g. a central processing unit (CPU) and/or a graphics processing unit (GPU)), a main memory 604, a static memory 606, and a drive unit 608 for mass data storage comprised of machine readable media 620. The computer system 600 can also include input/output devices 610, a display unit 612 (e.g. a liquid crystal display (LCD), a solid state display, or a cathode ray tube (CRT)), and a network interface device 614. Communications among these various components can be facilitated by means of a data bus 618. One or more sets of instructions 624 can be stored completely or partially in one or more of the main memory 604, static memory 606, and drive unit 608. The instructions can also reside within the processor 602 during execution thereof by the computer system. The input/output devices 610 can include a keyboard, a mouse, a multi-touch surface (e.g. a touchscreen) and so on. The network interface device 614 can be comprised of hardware components and software or firmware to facilitate wired or wireless network data communications in accordance with a network communication protocol.

The drive unit 608 can comprise a machine readable medium 620 on which is stored one or more sets of instructions 624 (e.g. software) which are used to facilitate one or more of the methodologies and functions described herein. The term "machine-readable medium" shall be understood to include any tangible medium that is capable of storing instructions or data structures which facilitate any one or more of the methodologies of the present disclosure. Exemplary machine-readable media can include magnetic media, solid-state memories, optical-media and so on. More particularly, tangible media as described herein can include; magnetic disks; magneto-optical disks; CD-ROM disks and DVD-ROM disks, semiconductor memory devices, electrically erasable programmable read-only memory (EEPROM)) and flash memory devices. A tangible medium as described herein is one that is non-transitory insofar as it does not involve a propagating signal.

Computer system 600 should be understood to be one possible example of a computer system, which can be used in connection with the various embodiments. However, the embodiments are not limited in this regard and any other suitable computer system architecture can also be used without limitation. Dedicated hardware implementations including, but not limited to, application-specific integrated circuits, programmable logic arrays, and other hardware devices can likewise be constructed to implement the methods described herein. Applications that can include the apparatus and systems of various embodiments broadly include a variety of electronic and computer systems. Some embodiments may implement functions in two or more specific interconnected hardware modules or devices with related control and data signals communicated between and through the modules, or as portions of an application-specific integrated circuit. Thus, the exemplary system is applicable to software, firmware, and hardware implementations.

Figure 7:
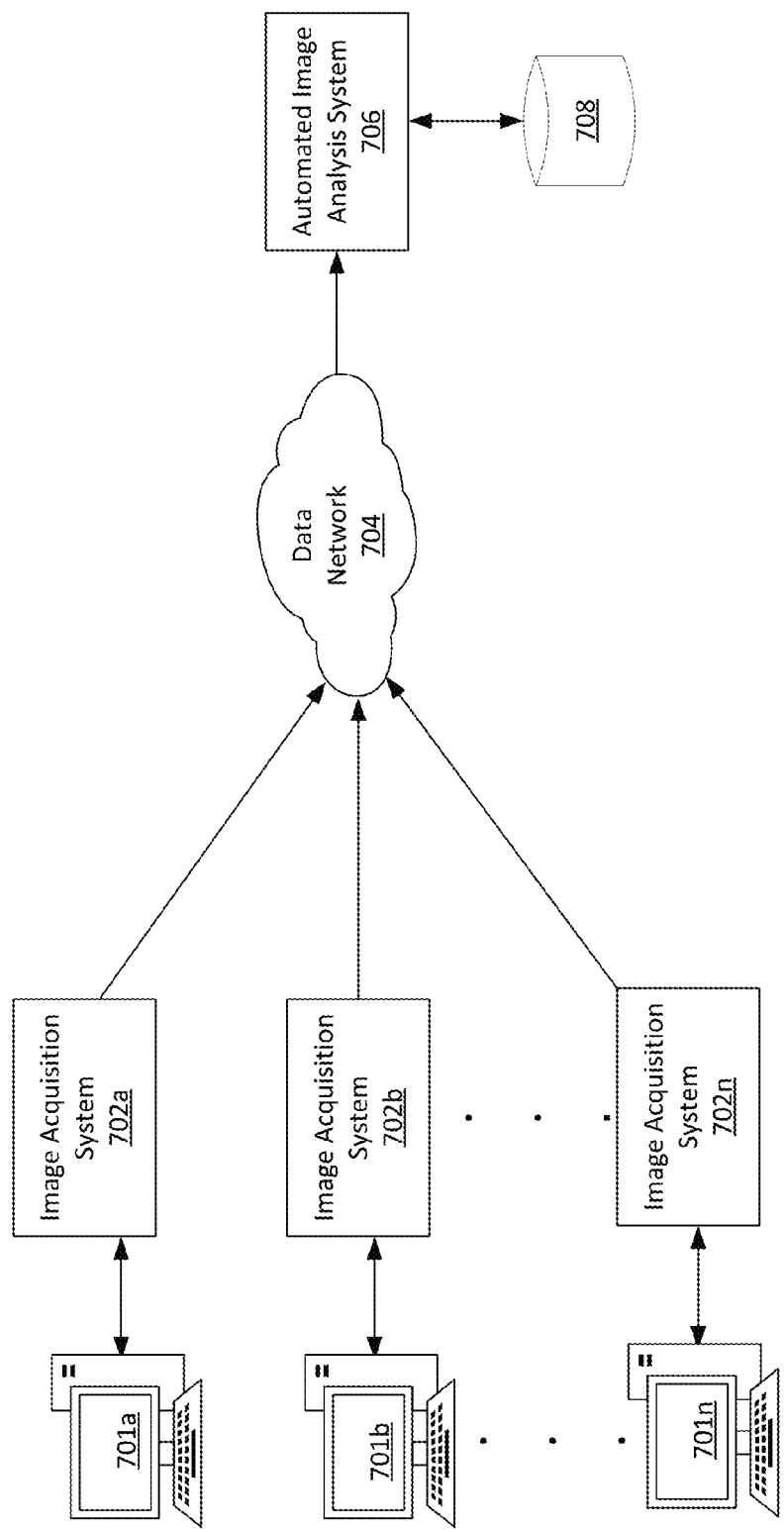
FIG. 7 is a block diagram that is useful for understanding a physical data acquisition step associated with the methods disclosed herein.

Referring now to FIG. 7, the automated analysis described herein begins with the acquisition of medical image data obtained by a non-invasive image acquisition system 702a, 702b . . . 702n. The medical image obtained using such systems can comprise a 2D or 3D image showing the cardiovascular structure. As is known, the image will be comprised of an array of elements called pixels (in the case of conventional 2D medical imaging) or voxels (in the case of conventional 3D medical imaging). Control of the non-invasive image acquisition systems 702a, 702b, . . . 702n can be facilitated by a respective workstation 701a, 701b, . . . 701n which allows a technician or practitioner to control the operation of the imaging system.

The medical imaging described herein can be acquired by a variety of different commonly used medical imaging modalities such as 2D and 3D echocardiography, magnetic resonance imaging, computed tomography, and/or nuclear medicine scans. These types of imaging systems are well-known in the art and therefore will not be described here in detail. However, it should be appreciated that regardless of the particular modality, each pixel or voxel comprising a particular image is obtained by means of a sampling or reconstruction process associated with the particular imaging technology. In general, such methods can be understood as processes which map numerical values to positions of the imaged space where the tissue of interest resides.

Of course, the actual value assigned to a voxel or pixel in such scenarios is a function of the particular imaging modality selected. Other factors which can affect such values can include the particular image reconstruction method used and any post-processing steps that are applied to the acquired images. It will be appreciated in this regard that both CT and MRI are popular in non-invasive assessment of cardiovascular diseases (CVDs). The resulting image data can be presented in a variety of data formats. For MINC (Medical Imaging NetCDF) and Digital Imaging and Communications in Medicine (DICOM) are two well-known examples.

The output image data from one or more image acquisition system 702a, 702b, . . . 702n is communicated to an automated image analysis system. Suitable metadata can be included with such imaging to identify the patient associated with such imaging. The automated image analysis system can be comprised of a deep-learning CNN architecture a described as described herein with respect to FIGS. 1-5.

The automated image analysis system 706 can comprise a server computer or other type of computer processing system, including cloud-based computing. As such, the automated image analysis system 706 can in some scenarios have an arrangement similar to processing system 600 as shown in FIG. 6. The image data acquired by the image acquisition systems 702a, 702b, . . . 702n can be communicated to the automated image analysis system 706 by means of a computer data network 704. The received image data can be stored in a suitable data storage, device such as a HIPAA-compliant data store 708 or HIPAA-compliant cloud-based store, to facilitate the image analysis processing steps described herein.

Further, it should be understood that embodiments can take the form of a computer program product on a tangible computer-usable storage medium (for example, a hard disk or a CD-ROM). The computer-usable storage medium can have computer-usable program code embodied in the medium. The term computer program product, as used herein, refers to a device comprised of all the features enabling the implementation of the methods described herein. Computer program, software application, computer software routine, and/or other variants of these terms, in the present context, mean any expression, in any language, code, or notation, of a set of instructions intended to cause a system having an information processing capability to perform a particular function either directly or after either or both of the following: a) conversion to another language, code, or notation; or b) reproduction in a different material form.

Figure 8:
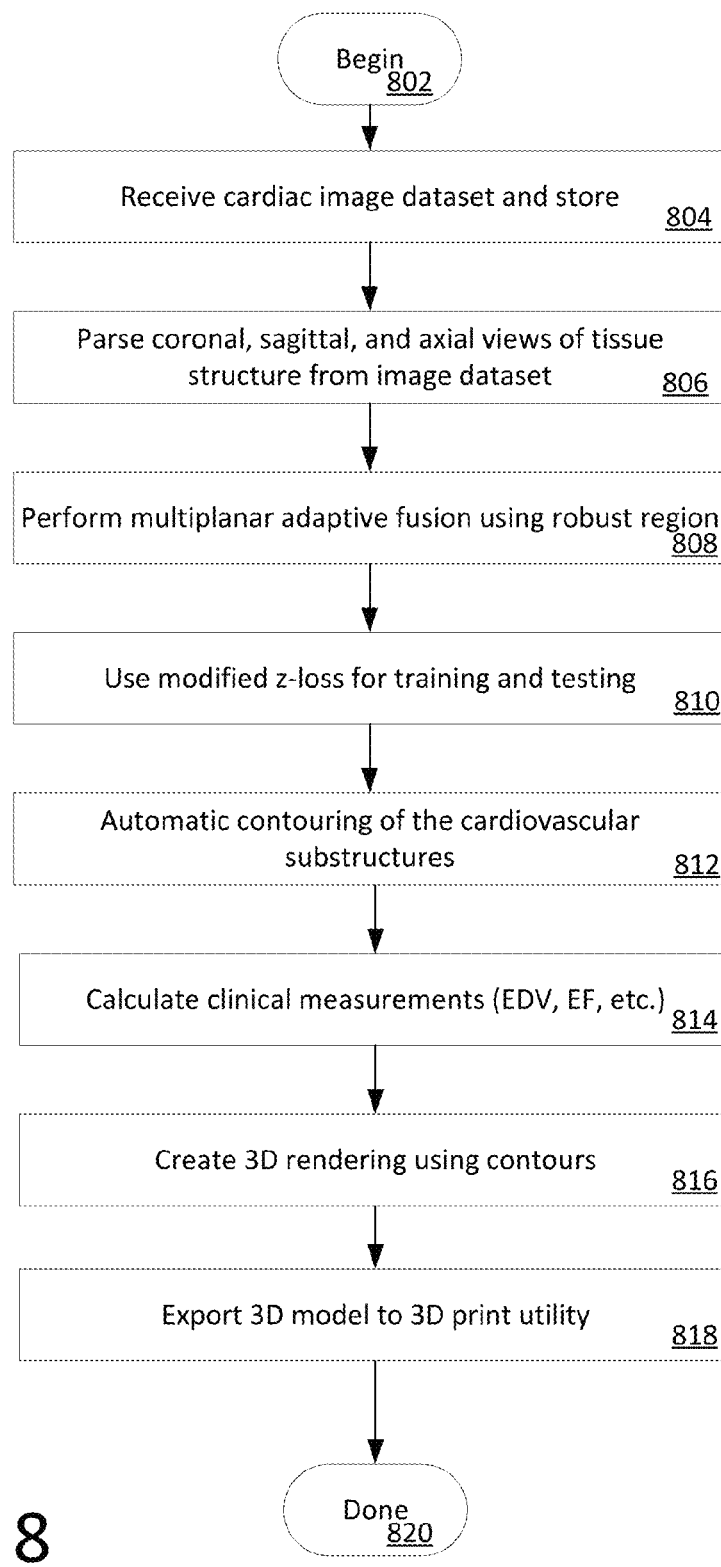
FIG. 8 is a flowchart which is useful for understanding an automated assessment process using the system disclosed herein.

Referring now to FIG. 8 there is a process flow diagram that is useful for understanding the present solution. The process begins at 802 and continues on to 804 where a cardiovascular image dataset is received and stored. At 806, coronal, sagittal and axial views are parsed from the dataset. Thereafter, at 808, the multiplanar adaptive fusion process is applied, using robust region processing as described herein. The modified z-loss function is used at 810 to provide fast convergence of network parameters. Upon completion of the segmentation process, the system performs automatic contouring of the various cardiovascular substructures at 812. Based on the results of such automatic contouring, the system automatically calculates the necessary clinical measurements (EDV, EF, and so on) at 814.

At steps 816 and 818 the results of the automated contouring described above can be optionally applied to 3D printing. 3D printing requires extremely accurate contouring of the structure of interest. When this precise form of contouring is manually performed, the process can take many hours to complete. With the solution disclosed herein, the resulting 3D volume can be reconstructed or rendered at 816 to form a virtual 3D model. More particularly, a virtual 3D rendering can be created of a cardiovascular substructure at 816 by using the contours from 312 and any standard 3D surface rendering technique. Such rendering techniques are well-known in the art and therefore will not be described here in detail. The resulting data file can then be exported at 318 as a 3D model (in a file format such as an OBJ or STL) to a 3D print utility (such as MakerWare™). At 820 the process terminates or the system continues on to perform other processing.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussions of the features and advantages, and similar language, throughout the specification may, but do not necessarily, refer to the same embodiment.

Furthermore, the described features, advantages and characteristics disclosed herein may be combined in any suitable manner in one or more embodiments. One skilled in the relevant art will recognize, in light of the description herein, that the embodiments can be practiced without one or more of the specific features or advantages of a particular embodiment. In other instances, additional features and advantages may be recognized in certain embodiments that may not be present in all embodiments.

Reference throughout this specification to "one embodiment", "an embodiment", or similar language means that a particular feature, structure, or characteristic described in connection with the indicated embodiment is included in at least one embodiment. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

Although the embodiments have been illustrated and described with respect to one or more implementations, equivalent alterations and modifications will occur to others skilled in the art upon the reading and understanding of this specification and the annexed drawings. In addition, while a particular feature of an embodiment may have been disclosed with respect to only one of several implementations, such feature may be combined with one or more other features of the other implementations as may be desired and advantageous for any given or particular application. Thus, the breadth and scope of the embodiments disclosed herein should not be limited by any of the above described embodiments. Rather, the scope of the invention should be defined in accordance with the following claims and their equivalents.

I claim:

1. A method for automated machine analysis of medical imaging, comprising:
using a computing system comprising at least one electronic processor circuit to
access from a data storage device, or cloud-based storage, complementary image data of a biological tissue structure (BTS) obtained by using a medical image acquisition system, the complementary image data comprising a plurality of two-dimensional images, obtained from a three-dimensional or two-dimensional dataset, which represent different views of the BTS respectively aligned with a plurality of distinct image planes;
process each of the plurality of two-dimensional images respectively using one of a plurality of separate convolutional neural networks (CNNs) instantiated by the computing system;
determine as a result of the processing performed by each CNN a probability map for one of the plurality of two-dimensional images which specifies for each pixel contained therein a probability that the pixel belongs to one of a plurality of pre-defined object classes; and
adaptively fuse the probability maps produced in each of the plurality of separate CNNs to produce a segmented output representative of the BTS.

2. The method according to claim 1, wherein the BTS is a cardiovascular tissue structure.

3. The method according to claim 2, further comprising using the segmented output representative of the cardiovascular structure to automatically perform a contouring operation to delineate a contour of at least one cardiovascular substructure.

4. The method according to claim 3, further comprising automatically calculating at least one clinical measurement based on the contour.

5. The method according to claim 3, further comprising automatically creating a 3D volume of the at least one cardiovascular substructure to facilitate fabrication of a physical 3D model using 3D printing.

6. The method according to claim 1, wherein the plurality of two-dimensional images are respectively aligned with a plurality of different imaging planes.

7. The method according to claim 6, wherein the plurality of two-dimensional images comprise an axial projection, a sagittal projection and a coronal projection.

8. The method according to claim 7, wherein the adaptively fusing comprises selectively varying the influence of each probability map as applied to the fusion process in accordance with the degree of reliability accorded to the probability map.

9. The method according to claim 7, further comprising automatically determining with the computing system the degree of reliability during a training stage of the CNN, without the need for ground truth.

10. The method according to claim 9, wherein the degree of reliability during the training stage is automatically determined by the computing system based on a connected component analysis.

11. The method according to claim 1, further comprising independently training each of the plurality of CNNs using a plurality of two-dimensional training images, each respectively corresponding to a predetermined image plane for which the CNN is to be utilized.

12. The method according to claim 11, further comprising facilitating a fast and reliable convergence of network parameters during the training by using a modified z-loss type of loss function.

13. The method according to claim 11, further comprising obtaining the plurality of two-dimensional training images respectively by parsing a plurality of image slices from a plurality of three-dimensional image volumes.

14. The method according to claim 13, wherein the plurality of two-dimensional training images are selected from one of an axial, sagittal, and coronal projection.

15. The method according to claim 14, further comprising augmenting the plurality of two-dimensional training images by using at least one of a translation and angular rotation operation to parse two-dimensional training images which vary with respect to the axial, sagittal and coronal projections.

16. The method according to claim 1, further comprising acquiring the complementary image data using a medical image acquisition system selected from the group consisting of 2D and 3D echocardiography, magnetic resonance imaging, computed tomography, and/or nuclear medicine scans.

17. A system for automated machine analysis of medical imaging, comprising:
a computing system comprising at least one electronic processor configured to
access from a data storage device, or cloud-based storage, complementary image data of a biological tissue structure (BTS) obtained by using a medical image acquisition system, the complementary image data comprising a plurality of two-dimensional images, obtained from a three-dimensional or two-dimensional dataset, which represent different views of the BTS respectively aligned with a plurality of distinct image planes;
process each of the plurality of two-dimensional images respectively using one of a plurality of separate convolutional neural networks (CNNs) instantiated by the computing system;
determine as a result of the processing performed by each CNN a probability map for one of the plurality of two-dimensional images which specifies for each pixel contained therein a probability that the pixel belongs to one of a plurality of pre-defined object classes; and
adaptively fuse the probability maps produced in each of the plurality of separate CNNs to produce a segmented output representative of the BTS.

18. The system according to claim 17, wherein the BTS is a cardiovascular tissue structure.

19. The system according to claim 18, wherein the computing system is configured to use the segmented output representative of the cardiovascular structure to automatically perform a contouring operation to delineate a contour of at least one cardiovascular substructure.

20. The system according to claim 19, wherein the computing system is configured to automatically calculate at least one clinical measurement based on the contour.

21. The system according to claim 17, wherein the plurality of two-dimensional images are respectively aligned with a plurality of different imaging planes.

22. The system according to claim 21, wherein the plurality of two-dimensional images comprise an axial projection, a sagittal projection and a coronal projection.

23. The system according to claim 22, wherein the adaptively fusing is configured to selectively vary the influence of each probability map as applied to the fusion process in accordance with the degree of reliability accorded to the probability map.

* * * * *